United States Patent [19]
Kensey et al.

[11] Patent Number: 5,531,759
[45] Date of Patent: Jul. 2, 1996

[54] SYSTEM FOR CLOSING A PERCUTANEOUS PUNCTURE FORMED BY A TROCAR TO PREVENT TISSUE AT THE PUNCTURE FROM HERNIATING

[75] Inventors: Kenneth Kensey, Chester Springs; John E. Nash, Downington; Douglas Evans, Devon, all of Pa.

[73] Assignee: Kensey Nash Corporation, Exton, Pa.

[21] Appl. No.: 235,825

[22] Filed: Apr. 29, 1994

[51] Int. Cl.$^6$ .................................................. A61B 17/04
[52] U.S. Cl. ............................ 606/213; 606/215; 604/15
[58] Field of Search ..................................... 606/139, 213, 606/215, 216, 228, 230

[56] References Cited

U.S. PATENT DOCUMENTS

| | | | |
|---|---|---|---|
| 4,946,468 | 8/1990 | Li . | |
| 5,021,059 | 6/1991 | Kensey et al. | 606/232 |
| 5,053,046 | 10/1991 | Janese | 606/215 |
| 5,222,974 | 6/1993 | Kensey et al. | 606/213 |
| 5,282,827 | 2/1994 | Kensey et al. | 606/215 |
| 5,312,435 | 5/1994 | Nash et al. | 606/213 |
| 5,342,393 | 8/1994 | Stack | 606/215 |
| 5,417,699 | 5/1995 | Klein et al. . | |

FOREIGN PATENT DOCUMENTS

WO89/11301 11/1989 WIPO .
WO94/13211 6/1994 WIPO .

*Primary Examiner*—Gary Jackson
*Attorney, Agent, or Firm*—Caesar, Rivise, Bernstein, Cohen & Pokotilow, Ltd

[57] ABSTRACT

A system and method for sealing a percutaneous puncture extending into internally located tissue, e.g., the peritoneum, of a living being. The system includes a reinforcing device and a deployment instrument. The device comprises a substantially rigid anchor, a resorbable holding member, a collagen plug, and a resorbable thin filament connecting the anchor, holding member, and plug in a pulley-like arrangement. The anchor or the plug or both may be formed of a resorbable material having a non-resorbable mesh reinforcement embedded therein. The deployment instrument includes a tubular carrier in which the closure and a tamping member are located. The tamping member is operated to expel the closure so that the anchor is in the interior of the peritoneum and the plug and the holding member are in the puncture tract, with both ends of the filament extending out of the puncture and with the holding member fixedly secured to a portion of the filament adjacent one end. The other end of the filament is then drawn proximally while the tamping is pushed distally to draw the anchor member against the tissue contiguous with the opening. The tamper mechanically deforms the plug within the tract. The extending ends of the filament are formed into a knot, a portion of which extends through the skin contiguous with the puncture, to lock the closure in place. The reinforced mesh of the closure reinforces any scar tissue which forms at the opening.

61 Claims, 5 Drawing Sheets

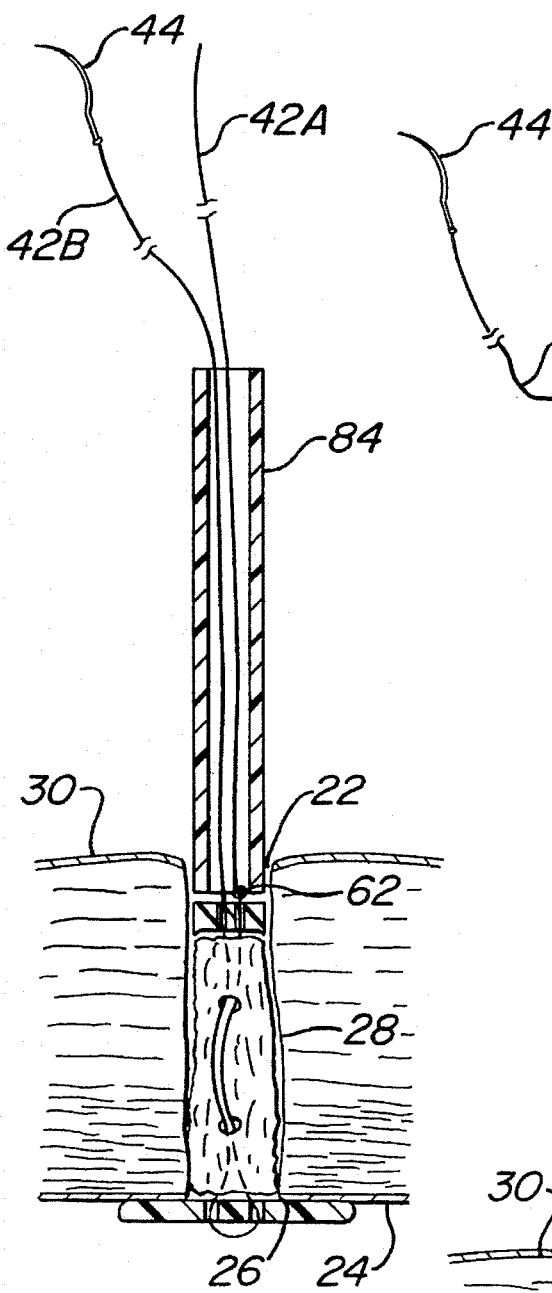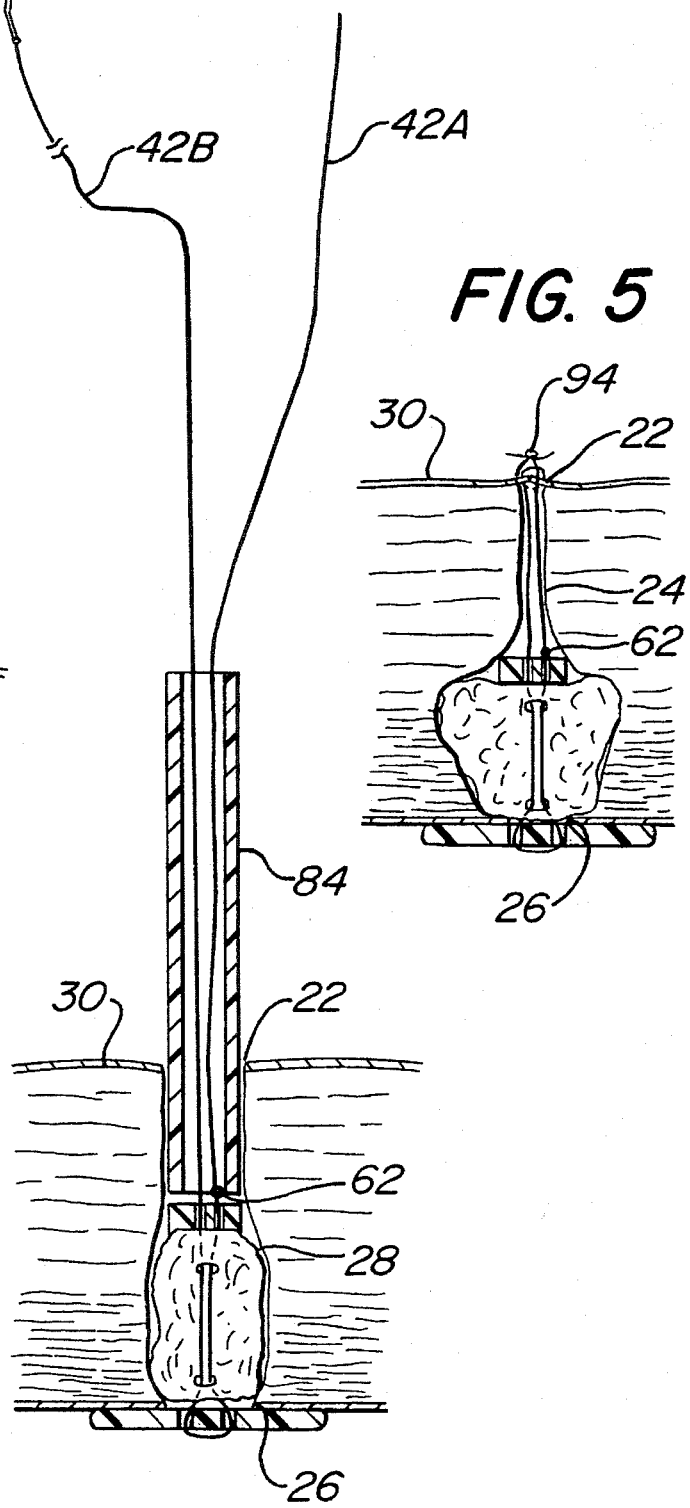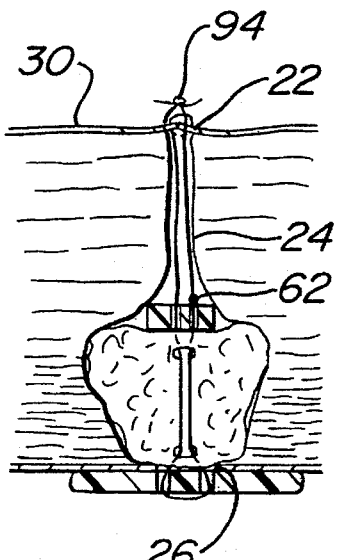

SYSTEM FOR CLOSING A PERCUTANEOUS PUNCTURE FORMED BY A TROCAR TO PREVENT TISSUE AT THE PUNCTURE FROM HERNIATING

This application relates generally to laparoscopic surgical procedures, and more particularly to a system and method for sealing the percutaneous puncture formed by a trocar during such procedures in order to prevent tissue contiguous with the puncture from herniating thereafter.

BACKGROUND OF THE INVENTION

A hernia is one of the most common ailments of mankind. Basically, a hernia is a weakness or hole in the abdominal wall through which abdominal contents such as bowels may protrude. In general, it relates to the abnormal protrusion of an organ or part of an organ or a portion of tissue through an aperture in its containing cavity. The usual, but not the only, hernia that is typically treated is congenital in origin, called an indirect inguinal hernia, and is due to the failure of the inner lining of the abdomen, called the peritoneum, to seal itself at the opening of the inguinal canal. Inguinal or groin hernias normally occur at one or more of three locations. The first location is in the weakened wall of the inguinal floor of the abdomen in Hesselback's triangle. This type of hernia is called a direct hernia. The second type of hernia is an indirect hernia that occurs at the internal ring adjacent to the vas deferens as it exits the abdomen to become part of the spermatic cord. The third type is a femoral hernia that occurs adjacent and medial to the femoral blood vessels. All hernias represent a potentially life threatening condition and once diagnosed they should be repaired unless there is some contraindication.

There are several different traditional surgical techniques for closing a hernial defect. The surgical repair of an inguinal hernia is a common procedure which surgeons often perform on an outpatient basis. This procedure entails making a formal 3 to 6 inch incision directly adjacent to the hernial defect. The various layers of tissue are cut and pealed back as the hernia area is dissected. This cutting through so many layers of tissue may be extremely traumatic. Moreover, such large incisions require careful post operative care to prevent infection from the outside. Other disadvantages of the conventional hernia surgery are the extended recuperation time and a large unsightly scar. Many other complications are possible: those related to any incision, such as bleeding and infection, and those related to conventional hernia procedures, such as damages to bowel and bladder, nerves and large blood vessels.

A less invasive surgical procedure to repair hernias has been used in conjunction with a laparoscope. Typically a prosthetic patch is inserted down the length of a trocar and forced out of the tube and moved into a desired position. Post-operative problems are decreased by this procedure because of the smaller external wound left by the surgical tube. The patch, however, still can shift before tissue has grown onto it. The patch also can be sutured to the transversalis fiasco or peritoneum to minimize movement. It has typically been difficult to attach patches with sutures using the laparoscope because of difficulties in viewing and in maneuvering through the laparoscope. Thus, while the laparoscopic techniques for hernia repair have generally proven to be less invasive, they still leave something to be desired from the standpoint of effectiveness.

In addition to hernias that are congenital in origin, such as an indirect inguinal hernia, it has been found that external trauma as well as surgical intervention can lead to the formation of hernias. In this regard, it has been found that laparoscopic surgery, itself, can lead to a number of both local and general complications, such as herniation at the site of the percutaneous laparoscopic puncture with or without the formation adhesions thereat. In fact, it is estimated that herniation occurs in an appreciable percentage of these procedures within several months of the procedure. The herniation occurs because the muscle tissue at the location of the puncture is damaged during the procedure. This muscle tissue then weakens and due to internal pressure the intestines or other organs of the abdominal cavity are pushed through this weakened area. Such muscle failure results in a direct hernia, the repair of which typically requires a synthetic mesh to reinforce the damaged muscle tissue.

In U.S. Pat. No. 5,254,133 (Seid) there is disclosed a surgical implantation device arranged to be placed within a patient's body to seal an existing hernial rupture. The device is arranged to be used with a laparoscope to minimize the external wound necessary. The implantation device is arranged to be compressed into an implanting condition for placement at the opening in the transversalis fascia from the interior of the peritoneum using a laparoscope and then to be expanded into a deployed condition to securely seal the opening. The peritoneum can either be left intact and pushed through the fascia opening by the surgical tube and held in place by the surgical implant device at the peritoneum, or can be pierced and the surgical tube and device can be positioned directly in the fascia opening.

While the device of the Seid patent appears to overcome some of the short fallings of traditional surgical hernia repair by introducing the device into the abdominal cavity through a laparoscopic port and then positioned from the inside of the peritoneum outward to treat an existing inguinal hernia, it never the less has its own shortcomings. In this regard one shortcoming of the Seid device is that the laparoscopic procedure utilized to introduce the device for the repair of another hernia, is likely to become a site of a future herniation.

Other prior art relating to the use of reinforcing materials to be implanted at the site of weakened internal tissue to prevent herniation, are found in U.S. Pat. Nos. 5,092,884 (Devereux et al.); 5,116,357 (Eberbach); 5,141,515 (Eberbach); 5,220,928 (Oddsen et al.); 5,290,217 (Campos); and 5,274,074 (Tang et al.) but none of these are deemed to be suitable for effecting the prevention of post-laparoscopic herniation in a percutaneous puncture.

Thus, a need presently exists for a device and technique to assist in the prevention of post-laparoscopic puncture herniation and eliminate the need for future surgical intervention.

In U.S. Pat. No. 5,021,059, which has been assigned to the same assignee as this invention, and whose disclosure is incorporated by reference herein, there is disclosed a closure device and method of use for sealing a small incision or puncture in tissue separating one portion of the body of a living being from another portion thereof, e.g., a percutaneous puncture in an artery, to prevent the flow of a body fluid, e.g., blood, through the puncture. The closure device is arranged to be used with (deployed by) an instrument which comprises a carrier in the form of a tubular member. The tubular member has a proximally located portion and a distally located portion. The latter includes an open free end arranged to be introduced through the incision or puncture. The proximately located portion of the tubular member is arranged to be located out of the body of the being when the distally located portion is extended through the incision or puncture. The closure device comprises three components, namely, an anchor member, a sealing member, and a filament, e.g., suture. The anchor member includes a tissue engaging portion configured to pass through the puncture in one direction but resistant to passage therethrough in the opposite direction. The sealing member is formed of a hemostatic material, such as compressed collagen foam, and has a tissue engaging portion. The filament is connected between the anchor member and the sealing member in a pulley-like arrangement so that they may be moved relative to each other by the application of a pulling force on the filament. The instrument is arranged to expel the anchor member through the puncture, e.g., into the artery, and to draw its tissue engaging portion into engagement with the tissue contiguous with the puncture. The filament extends through the instrument to a point outside the body of the being and is arranged to be drawn in the proximal direction, whereupon the portion of the filament connecting the anchor member causes the tissue engaging portion of the sealing member to move with respect to the anchor member, thereby drawing the anchor member and sealing member together. This action causes the tissue engagement portion of the sealing member to seal the puncture from the flow of fluid therethrough.

In copending U.S. patent application Ser. No. 07/846,322, filed on Mar. 5, 1992, entitled Hemostatic Puncture Closure System and Method of Use, also assigned to the same assignee as this invention, and whose disclosure is incorporated by reference herein, there is disclosed and claimed an improved system for sealing a percutaneous puncture in a blood vessel of a living being, with the puncture comprising an opening in the wall of the blood vessel and a tract contiguous with that opening and extending through tissue overlying the blood vessel. That system basically comprises carrier means, introducer means, and closure means. The closure means comprises anchoring means, sealing means, and filament means, with the filament means coupling the anchoring means and the sealing means. The introducer means comprises a tubular member having a distal free end insertable into the puncture tract and through the opening in the blood vessel wall. The carrier means is insertable through the introducer means and includes means to expel the anchoring means therefrom. Moreover, the carrier means is retractable with respect to the introducer means after the anchoring means has been expelled from the carrier means, so that when it is retracted it draws the anchoring means into engagement with the distal free end of the introducer means. The introducer means and the carrier means are coupled for movement together to draw the anchoring means which is now in engagement with the distal end of the introducer means into engagement with the interior tissue of the vessel generally adjacent the opening in the wall thereof. The filament means is operative to move the anchoring means and the sealing means relative to each other to cause the sealing means to engage tissue generally adjacent the puncture outside of the vessel.

In yet another copending application, Ser. No. 08/012,816, filed on Feb. 3, 1993, entitled Hemostatic Vessel Puncture Closure System Utilizing A Plug Located Within The Puncture Tract Spaced From The Vessel And Method Of Use, which is assigned to the same assignee as this invention, and whose disclosure is incorporated by reference herein, there is disclosed a further improved puncture closure system. That system basically comprises carrier means, introducer means, and closure means. The puncture comprises a tract extending through tissue overlying the blood vessel. In the preferred embodiment, the closure device comprises four components, namely, an anchor member, a sealing member, a spacer member, and a filament, e.g., suture. The anchor member includes a tissue engaging portion configured to pass through the puncture in one direction but resistant to passage therethrough in the opposite direction. The sealing member is formed of a hemostatic material, such as compressed collagen foam. The spacer member is mounted upon the suture, and is slidable thereon, and is positioned between the anchor member and the sealing member. The filament member is connected between the anchor member and the sealing member in a pulley-like arrangement so that the members may be moved relative to each other by the application of a pulling force on the filament. The instrument is arranged to expel the anchor member through the puncture, e.g., into the artery, and to draw its tissue engaging portion into engagement with the tissue contiguous with the puncture. The filament extends through the instrument to a point outside the body of the being and is arranged to be drawn in the proximal direction, whereupon the portion of the filament connecting the anchor member and the sealing member causes the sealing member to move with respect to said anchor member and into engagement with the spacer member thereby drawing the anchor member, spacer member and sealing member together. This action causes the sealing member to seal the puncture from the flow of fluid therethrough. The presence of the spacer member prohibits the sealing member from contacting the arterial wall and thereby possibly entering into the artery where a portion could conceivably break off and flow distally or cause the creation of an embolism.

In still another copending application, Ser. No. 08/064,192, filed on May 17, 1993, entitled Fail Predictable Reinforced Anchor For Hemostatic Closure, which is assigned to the same assignee as this invention, and whose disclosure is incorporated by reference herein, there is disclosed a further improved puncture closure system. In the preferred embodiment of the system specifically disclosed in that application the closure comprises an elongated rigid anchor member formed of a resorbable material, a sealing member formed of a resorbable material, e.g., compressed collagen plug, and a thin resorbable material filament, e.g., a suture, connecting the anchor member and the sealing member. The anchor member is located in the interior of the vessel, with the sealing member being located in the puncture tract. An elongated reinforcing filament or ribbon (either apertured or unapertured), formed of a resorbable material, is incorporated in the elongated anchor member to prevent any portion of it from breaking away in the event that the anchor is loaded beyond its breaking point.

It has been determined that the devices disclosed in the aforementioned applications, with some modifications, as well as other devices, some preferred embodiments of which are set forth hereinafter, can be used to effect the sealing of a percutaneous puncture formed during a laparoscopic procedure of the abdomen or an endoscopic procedure of the thoracic cavity in such a manner that the long-term strength of the scar tissue forming at the opening of the internally located tissue is enhanced, e.g., in the case of the puncture in the peritoneum the scar tissue is reinforced to render it resistant to herniation.

OBJECTS OF THE INVENTION

Accordingly, it is a general object of this invention to provide devices and methods of use which address the needs of the prior art to enhance the long-term strength of scar tissue formed at the site of an opening in a percutaneous puncture.

It is another object of this invention to provide a device and method of use for extension through a percutaneous puncture extending into the abdomen of a living being to increase the long-term strength of the scar tissue which forms at the peritoneum, and thereby render such tissue resistant to herniation.

It is another object of this invention to provide a device and method of use for extension through a percutaneous puncture extending into the abdomen of a living being to seal that puncture, increase the long-term strength of the scar tissue which forms at the peritoneum, and thereby render such tissue resistant to herniation.

It is yet another object of this invention to provide a device and method of use for extension through a percutaneous puncture extending into the thoracic cavity of a living being to seal that puncture from the leakage of air and to increase the long-term strength of the scar tissue which forms at the puncture.

It is still another object of this invention to provide a device for which is simple in construction and can be readily used in minimally invasive surgery to enhance the long-term strength of scar tissue formed at the site of an opening in a percutaneous puncture.

SUMMARY OF THE INVENTION

These and other objects of this invention are achieved by providing a system and a method for increasing the long-term strength of scar tissue forming at the opening of internally located tissue, e.g., the peritoneum, the lining of the thoracic cavity, created by a percutaneous puncture during minimally invasive, e.g., laparoscopic, endoscopic, arthroscopic, etc., surgery. The percutaneous puncture includes a puncture tract extending from the skin to the opening in the internally located tissue.

The system includes a deployment instrument and a device. The device includes means, e.g., reinforcing means, to improve the long-term strength of scar tissue forming at the opening in the tissue, and securement means for holding the device in place. The securement means comprises a first portion, e.g., an anchoring means, arranged to be extended through the tract and the opening for engaging the interior of the tissue, e.g., the peritoneum or the thoracic cavity lining, adjacent the opening to render the first portion resistant to passage back through the opening, and second means, e.g., plug means, located outside the tissue and coupled to said first means and cooperating therewith for holding the device in place within the puncture.

In accordance with one method aspect of the invention the device is introduced into the puncture by a deployment instrument forming a portion of the system. The deployment instrument includes tamping means for extension into the puncture tract to deform the second portion of the device, e.g., the plug means, so that it seals the puncture tract.

In accordance with another aspect of the invention the device includes filament means, and a holding member secured to the filament, with the filament means having a pair of ends extending out of the puncture for securement, e.g., knotting, together adjacent the skin to hold the device in place.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein:

FIG. 3 is a side elevational view like FIG. 2 but showing the subject invention at subsequent time, i.e., immediately after the removal of the deployment instrument and trocar from the percutaneous puncture leaving the device in place;

FIG. 4 is a side elevational view like FIG. 3 but showing the subject invention at yet a further time, i.e., when a tamping component of the deployment instrument is used to deform a portion of the device in the percutaneous puncture;

FIG. 5 is a side elevational view like FIG. 4 but showing the device of subject invention after it is fully installed within the percutaneous puncture;

FIG. 10 is an enlarged sectional view taken along line 10—10 of FIG. 1;

FIG. 11 is an enlarged sectional view taken along line 11—11 of FIG. 1;

FIG. 12 is an enlarged sectional view taken along line 12—12 of FIG. 1; and

DETAILED DESCRIPTION OF THE PREFERRED EMBODIMENT

Figure 1:
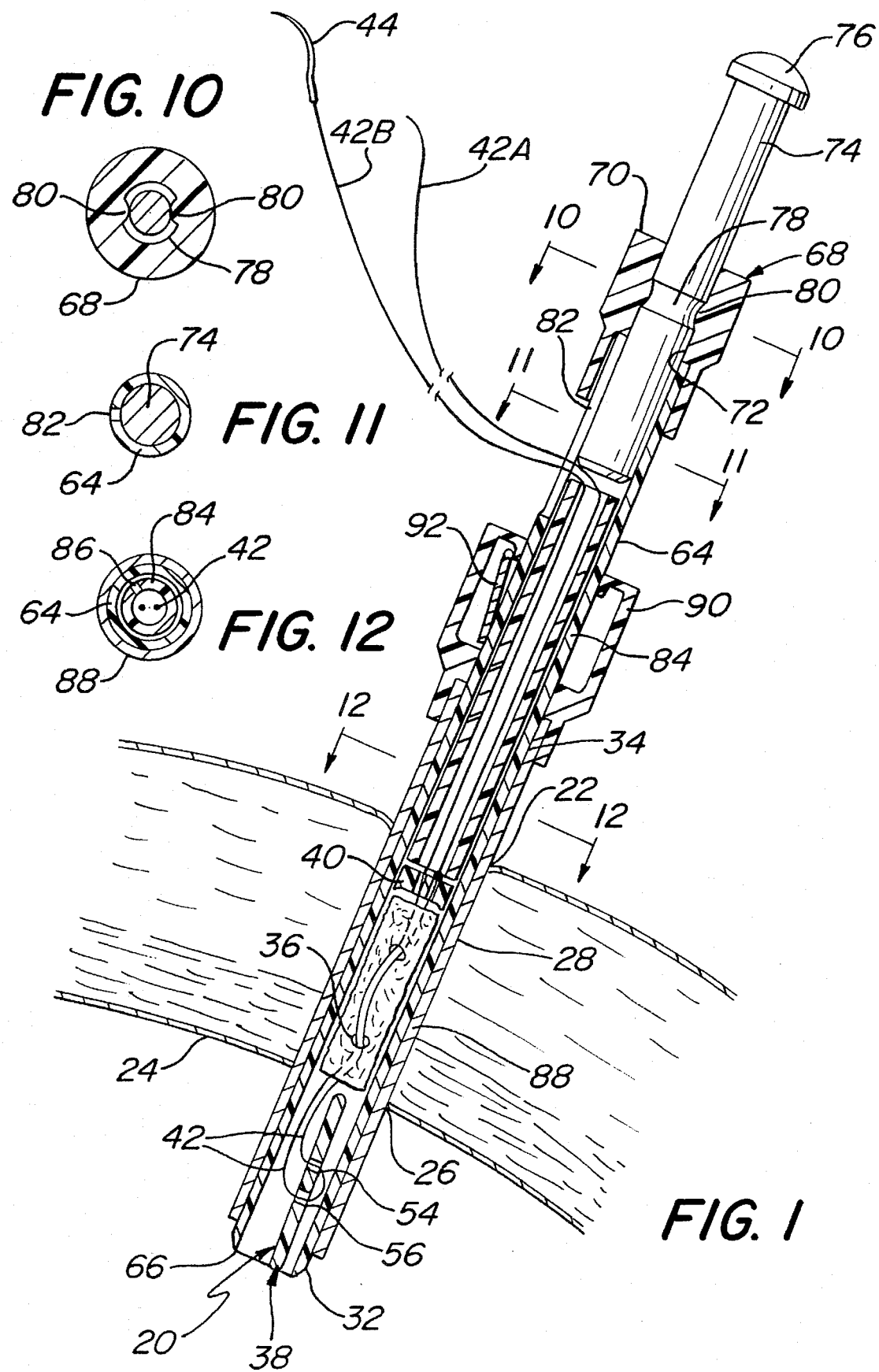
FIG. 1 is a side elevation view, partially in section, showing a trocar extending percutaneously into the abdomen of a living being, with a deployment instrument and a device of the system of the subject invention located therein for placement of the device into the percutaneous puncture.

Referring now in greater detail to the various figures of the drawings wherein like reference characters refer to like parts, there is shown at 20 a device constructed in accordance with this invention for disposition within a percutaneous puncture 22 extending into penetratable internal tissue. In the embodiment shown herein the penetratable tissue comprises the peritoneum or the lining of the thoracic cavity, and that tissue is designated by the reference number 24. The percutaneous puncture includes an opening 26 in the tissue and a tract 28 extending from the surface of the skin 30 to the opening through the underlying tissue, e.g., the fat/fascia and muscle.

It should be pointed out at this juncture that while the device 20 and its deployment instrument 32 have particular utility when used in connection with minimally invasive surgical procedures, it is to be understood that the subject invention can be used to reinforce or otherwise enhance the long-term strength of scar tissue which may form at any internal puncture site. Thus, while the description of the preferred embodiment instrument and device to follow is directed to the closing off of percutaneous incisions or punctures in the abdominal cavity or in the thoracic cavity, the subject invention has much more wide-spread applications.

As can be seen in FIG. 1 the device 20 is arranged to be extended into the puncture by means of a deployment instrument 32. The deployment instrument is arranged to be extended through a conventional or non-conventional trocar, in order to place the device 20 in position. The trocar is shown schematically in FIG. 1 and designated by the reference number 34. It should be noted at this point that in some applications the use of a trocar may be obviated so that the deployment instrument 32, per se, can be inserted through the puncture to place the device 20 in the desired position within the puncture.

In any case the device 20 is arranged to be deployed into the puncture by the deployment instrument 32 so that a first portion of it (to be described later) is extended through the opening 26 and makes contact with the adjacent, e.g., contiguous, tissue, while a second portion of it (also to be described later) is within the puncture tract 28 to seal the puncture tract from the flow of fluid therethrough. As will also be described later one or both of those portions of the device include means, e.g., reinforcing means, so that the long-term strength of scar tissue which will form at the opening 26 is improved, thereby making that scar tissue resistant to subsequent herniation.

Referring now to FIGS. 1, 6, 7, 8, 9, and 13, it will be seen that the device 20 basically comprises four components, namely, a sealing member 36, an anchoring member 38, a holding member 40, and a positioning filament 42. A standard, conventional, e.g., curved stainless steel, needle 44 is secured to one end of the filament, and thus, may be considered as a fifth component of the device 20. The function of the needle 44 will be described later.

Figure 9:
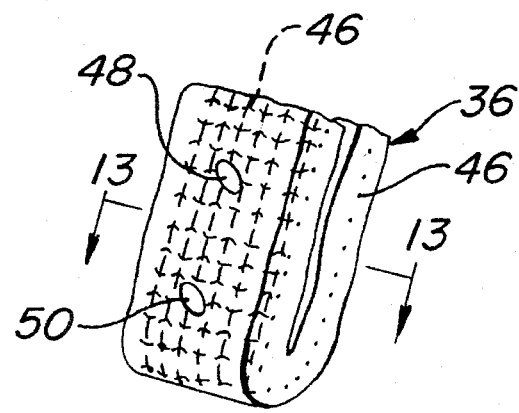
FIG. 9 is an enlarged isometric view of the plug component of the device of the subject invention.
Figure 13:
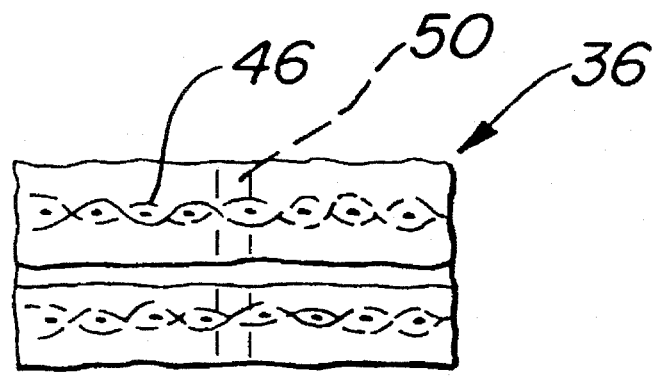
FIG. 13 is an enlarged sectional view taken along line 13—13 of FIG. 9.

The sealing member 36 is deformable and is arranged to be located within the puncture tract and deformed therein to seal the tract from the flow of fluid therethrough. As best seen in FIGS. 6, 7, 9, and 13 the sealing member 36 basically comprises a strip of a compressible, resorbable, collagen foam, such as that sold by Colla-Tec, Inc. of Plainsboro, N.J. 08536. The strip of collagen foam includes a thin web or strip of a non-resorbable, e.g., dacron, reinforcing mesh 46 embedded within it. The mesh 46 serves to aid in reinforcing the scar tissue which forms adjacent the opening 26 in the tissue wall 24 when the plug member is in place. It should be pointed out at this juncture that other reinforcing materials, e.g., resorbable suture materials such as that sold under the trademark DEXON by Davis+Geck of Wayne, N.J. 07470, can be used in the sealing member, if desired. The reinforcing materials can take various configurations, e.g., filaments, meshes, strips, bands, etc. In fact, if desired, it is contemplated that no reinforcing means be used in the sealing member 36, particularly if the anchoring member includes reinforcing means (to be described later). In the embodiment of the sealing member 36 shown herein the strip 36 is folded in two as shown in FIG. 9 and includes a pair of apertures 48 and 50 extending through the folded over strip. The apertures 48 and 50 are arranged to have portions of the filament 42 extended therethrough, as will be described later, to couple the various components of the device 20 to one another.

Figure 6:
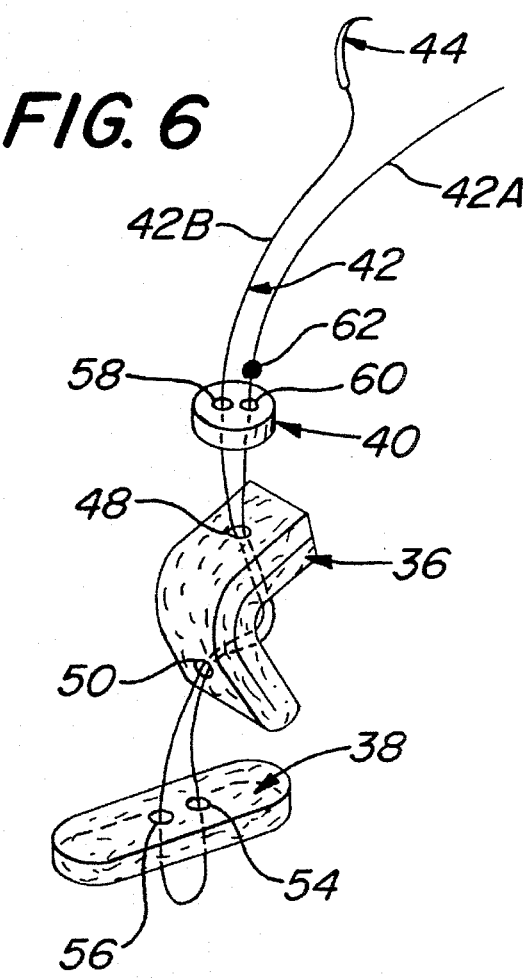
FIG. 6 is an isometric view of the device of the subject invention during its fabrication.
Figure 7:
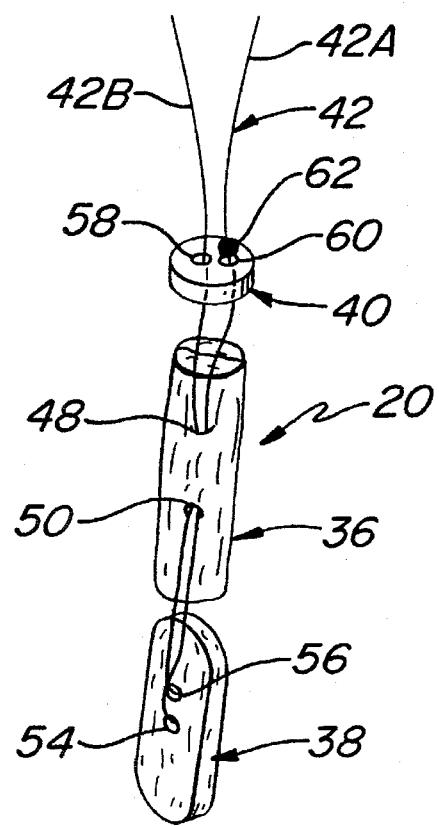
FIG. 7 is an isometric view like that of FIG. 6 but showing the device in its completed state ready for disposition within the deployment instrument shown in FIG. 1.

The folded over strip is arranged to be compressed from the state shown in FIG. 6 to that as shown in FIG. 7 so that the resultant plug member 36 is of reduced diameter, e.g., 8 mm, or width to fit within the deployment instrument as shown in FIG. 1.

Figure 8:
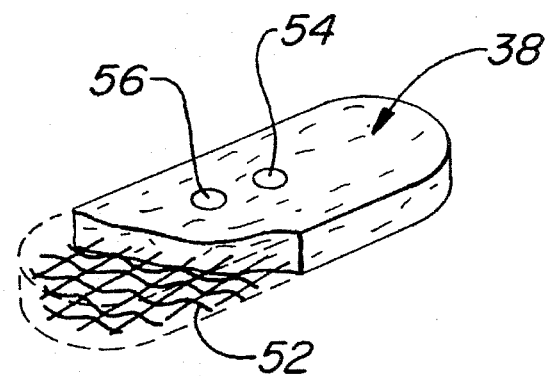
FIG. 8 is an enlarged isometric view, partially broken away, of the anchor component of the device of the subject invention.

The anchoring member 38 is arranged to be seated inside the penetrated internal structure, e.g., the peritoneum, against the tissue thereof adjacent, e.g., contiguous, with the opening 26 through which it had been introduced. As best seen in FIGS. 6–8 the anchoring member 38 is an elongated, low-profile component, similar to the anchor of the closure disclosed in the aforementioned copending patent applications, e.g., it may be formed of any resorbable material, such as a resorbable lactide/glycolide polymer sold by Medisorb Technologies International L.P. under the trade designation MEDISORB. The anchoring member is sufficiently rigid such that once it is in position within the abdominal cavity (as will be described later) it is resistant to deformation to preclude it from bending to pass back through the puncture through which it was first introduced.

In accordance with the preferred embodiment of the invention shown herein the anchoring member also includes reinforcing means, e.g., a strip or web 52 (FIG. 8) of a woven, non-resorbable mesh, such as dacron, embedded therein. The mesh serves to aid in reinforcing the scar tissue which forms adjacent the opening 26 in the tissue wall 24 when the anchoring member 38 is in place. It should be pointed out at this juncture that other reinforcing materials, e.g., resorbable suture materials such as that sold under the trademark DEXON by Davis+Geck of Wayne, N.J. 07470, can be used in the anchoring member, if desired. The reinforcing materials can take various configurations, e.g., filaments, meshes, strips, bands, etc. In fact, if desired, it is contemplated that no reinforcing means be used in the anchoring member, particularly if the sealing member includes reinforcing means (described earlier). In the embodiment of the invention wherein the anchoring member is reinforced it serves to reinforce any scar tissue which will form in the immediately adjacent tissue.

The anchoring member 38 includes a pair of apertures 54 and 56 extending through it. These apertures are arranged to have portions of the filament 42 extended therethrough, as will be described later, to couple the various components of the device 20 to one another.

As can be seen in FIGS. 6 and 7 the holding member 40 is a disk-like member having a pair of apertures 58 and 60 extending therethrough. In accordance with a preferred embodiment of this invention the member 40 is rigid or stiff and is resorbable, e.g., is formed of the same material as that of the anchoring member. The apertures 58 and 60 are arranged to have portions of the filament 42 extended therethrough, as will be described later, to couple the various components of the device 20 to one another.

The filament 42 preferably comprises a very thin flexible member, e.g., a resorbable suture, which connects the anchoring member 38, the sealing member 36, and the holding member 40 in a pulley-like arrangement. In particular the filament is threaded through the aperture 58 in the holding member 40, from there through the aperture 48 in the plug member from one side to the opposite side thereof and out the aperture 50, from there into the aperture 56 in the anchoring member, from there out of aperture 54 in the anchoring member, from there in through the aperture 50 in the plug member from one side to the opposite side thereof and out the aperture 48, from there through the aperture 60 in the holding member 40. This arrangement produces a pair of proximal end portions 42A and 42B. A knot 62 is provided in the end portion 42A of the filament immediately proximally of the aperture 60 in the holding member 40. The needle 44 is connected to the free end of end portion 42B.

As can be seen clearly in FIG. 1 the end portions 42A and 42B of the filament 42 are arranged to extend out of the deployment instrument 32 when the device 20 is disposed therein. Accordingly, as will be described later when the device 20 is deposited in the puncture 22 by the deployment instrument the end portions 42A and 42B of the filament 42 extend out of the puncture tract 28. This arrangement enables the filament 42 to be manipulated to effect the proper seating of the device in place. Moreover, the ends 42A and 42B are arranged to be secured together, e.g., knotted by a conventional surgical knot, penetrating the tissue contiguous with the opening in the skin after the device is properly seated within the puncture to aid in holding or locking the device in place.

If desired, one or more additives, such as a radiopaque material or hemostatic agent or antibacterial agent, or any other biologically active ingredient, can be blended into or coated upon the holding member, the anchoring member, the filament member, or the sealing member or any combination thereof.

Referring now to FIG. 1 the details of the deployment instrument 32 will now be described. As can be seen therein the deployment instrument basically comprises an elongated tube or carrier 64 having an open distal free end 66 and a plunger assembly 68 located at the proximal end. The device 20 is disposed within the hollow interior of the carrier tube 64 adjacent its open free end 66, with the anchoring member 38 located immediately adjacent the free end and oriented so that its longitudinal axis is parallel to the longitudinal axis of the carrier tube. The sealing member is located immediately proximally of the anchoring member, and the holding member is located immediately proximally of the sealing member.

The plunger assembly comprises a cylindrical cap 70 having a central passageway 72 extending therethrough in axial alignment and communicating with the interior of the tube 64. An elongated, cylindrical plunger 74 is located within the passageway 72 in the cap 70. The proximal end of the plunger is in the form of an enlarged head or button 76. An annular recess 78 is provided about the periphery of the plunger. A pair of diametrically opposed nibs 80 (FIG. 10) project from the inner surface of the cap into the annular recess to hold the plunger in a retracted, "ready" position as shown in FIG. 1. A longitudinally oriented slot 82 (FIG. 11) is provided in the carrier tube 64 adjacent the cap 70 to enable the ends 42A and 42B of the filament to extend out of the deployment instrument.

A tamping member 84, in the form of an elongated sleeve, is disposed within the hollow interior of the carrier tube 64 between the holding member 40 and the distal end of the plunger 74. The sleeve includes a thin slot 86 (FIG. 12) extending along the length of the sleeve. The tamping member, being an elongated sleeve includes a central passageway extending fully therethrough. The end portions 42A and 42B of the filament are arranged to extend through the central passageway in the tamping member 84, as shown clearly in FIGS. 1 and 2.

Figure 2:
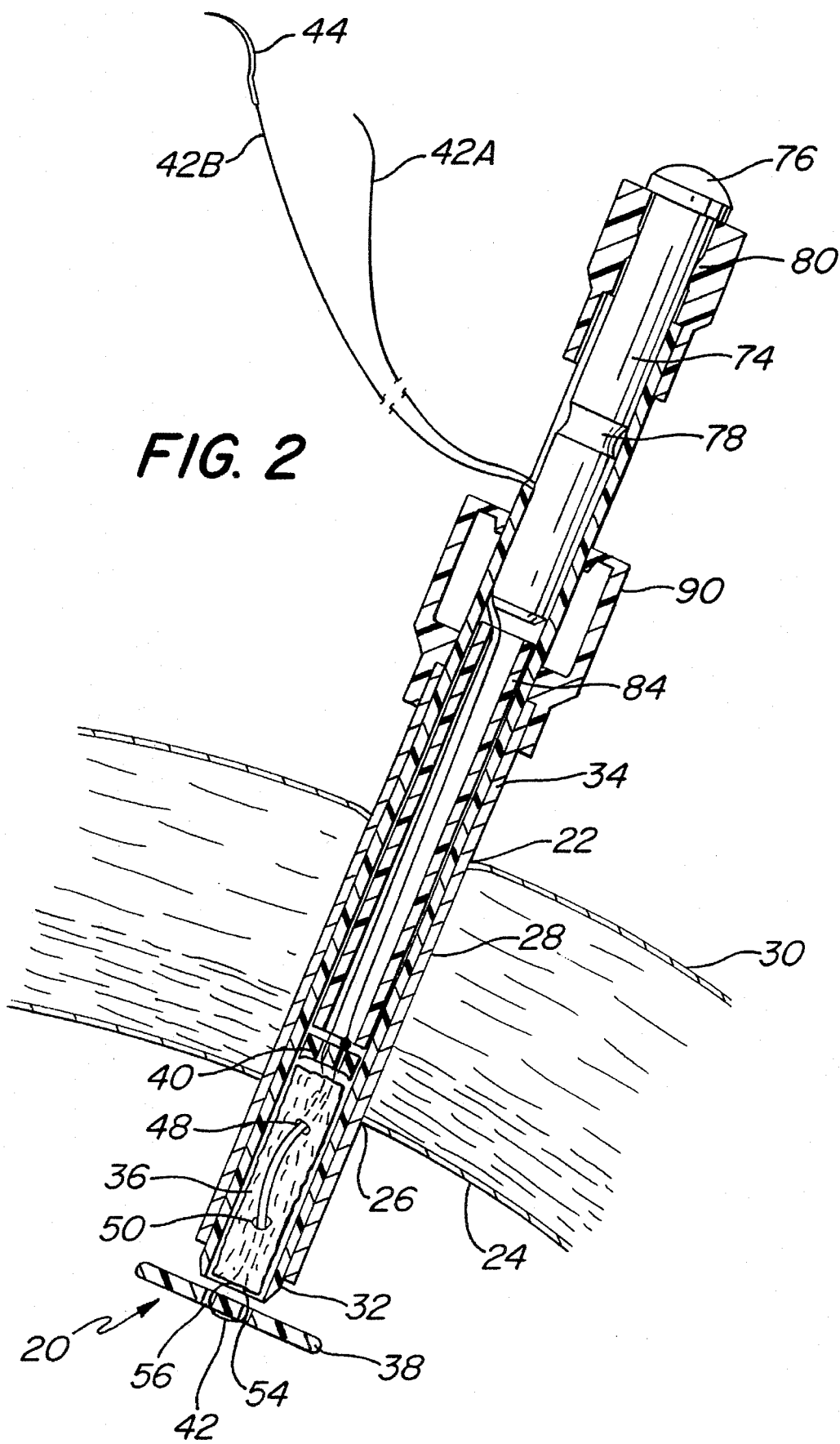
FIG. 2 is a side elevational view like FIG. 1 but showing the subject invention at an initial step in the ejection of a portion of the device from the deployment instrument.

As can be seen in FIG. 1 the trocar 34 basically comprises an elongated tube or sheath 88 formed of any suitable material, e.g., stainless steel. The sheath has an open distal end and a valve assembly 90 located at its proximal end. The valve assembly 90 includes any suitable valve member 92 to enable the deployment instrument to be inserted therethrough, as shown in FIGS. 1 and 2.

The device 20 of the subject invention is arranged to be used after the minimally invasive interventional procedure (e.g., laparoscopic, endoscopic, arthroscopic, procedure) is finished to enhance the long-term strength of the scar tissue which will naturally form at the opening 26 of the puncture 22 formed during the interventional procedure. To that end, the physician inserts the delivery or deployment instrument 32 containing the device 20 into the trocar 34 so that the distal end of the deployment instrument is extended through the opening 26 in the tissue wall as shown in FIG. 1. The plunger 74 of the deployment instrument is then depressed by pressing on its head or button 76 to release it from the ready position of FIG. 1 and move it distally, as shown in FIG. 2. This action causes the distal end of the plunger 74 to push on the proximal end of the tamping member 84, thereby moving the tamping member distally. This action, in turn, pushes on the holding member 40, the sealing member 36, and the anchoring member 38, to cause the anchoring member to pass out of the distal end of the instrument and trocar sheath, thereby deploying the anchoring member into the abdominal cavity.

The deployment instrument and trocar are then withdrawn from the puncture 22. This withdrawing action causes the anchoring member 38 to engage (e.g., catch) on the peritoneal wall contiguous with the opening 26. Continued withdrawal of the instrument and trocar deposit the sealing member 36, the holding member 40, and the distal end of the tamping member 84 of the deployment instrument into the puncture tract, as shown in FIG. 3. The tamping member is then grasped and gently pushed or tamped repeatedly into the puncture tract to push on the holding member. At the same time the free end of the filament 42 is pulled in the proximal direction. This combined action is shown in FIG. 4 and has the effect of moving the holding member 40 toward the anchoring member 38, thereby deforming the sealing member 36 therebetween. The knot 62 on the filament 42 adjacent the end portion 42A serves to hold the holding member 40 against the proximal end of the deformed sealing member.

As will be appreciated by those skilled in the art since the sealing member is formed of compressed collagen (or other hydrolytic material) it expands automatically in the presence of blood or body fluids within the puncture tract when deployed, thereby further contributing to its deformation, e.g., enlargement, within the puncture tract. In addition the expansion/deformation of the sealing member serves to aid in securing the device 20 in place. Thus, it is contemplated that in some applications the deformation/expansion of the sealing means will serve as the only or primary means for securing the device in place within the puncture.

Moreover, for some applications it is contemplated that the holding means 40 may be constructed like the compressible disk locking mechanism of the intravascular puncture closure disclosed in copending U.S. patent application Ser. No. 08/072,293, filed on Jun. 4, 1993, entitled A Hemostatic Vessel Puncture Closure With Filament Lock, which is assigned to the same assignee as this invention and whose disclosure is incorporated by reference herein. The puncture closure of that application includes an anchoring member, a sealing member or plug of collagen foam, the locking mechanism, and a filament. The filament connects the anchoring member located within the interior of an artery with the plug in the puncture tract in a pulley-like arrangement so that the plug is movable toward the anchoring member. The compressible disk locking mechanism is arranged to be actuated, e.g., compressed, within the puncture tract to engage the filament in such a manner that the plug is held in the puncture sealing position. It is also contemplated that the filament and the anchoring means of this invention can be constructed like those locking mechanism components of the aforementioned copending application, wherein the anchoring means includes a notched passageway through which the filament extends and the filament comprises a portion having plural projections or teeth thereon adapted to slide into the notched passageway of the anchoring means in one direction but resistant to sliding in the opposite direction.

In any case, when the sealing member is in place within the puncture tract as described above it has the effect of sealing the puncture tract from the flow of fluid therethrough. Thus, in the case of thoracic placement the sealing member will prevent ingress of air into or out of the thoracic cavity. In the case of peritoneal placement the sealing member will prevent the egress of blood or some other body fluid out of the abdominal wall.

Once the sealing member has been deformed and placed as just described, the tamping member 84 is then removed from the puncture tract 28. To that end the extending portions 42A and 42B of the filament 42 are slid through the tamping member's longitudinally extending slot 86, thereby freeing the tamping member from the device 20. The end portions 42A and 42B of the filament extending out of the puncture tract are then knotted together. In particular, using standard surgical techniques, the filament end 42B with the stainless steel needle 44 is used to suture the skin 30 surface contiguous with the puncture 22 to form a conventional surgical knot 94 and thereby secure the device in place.

As will be appreciated by those skilled in the art the timing of the resorption of the resorbable components of the device 20 can be controlled by various means, e.g., the higher the molecular weight of the resorbable polymer, the longer the material will take to resorb.

It should be pointed out at this juncture that the device of the subject invention can be used to repair an existing hernia. To that end the existing hernia can be penetrated from the outside by means of any suitable piercing instrument, e.g., a conventional or non-conventional trocar, to form a percutaneous puncture through the herniated tissue. Once this has been accomplished the device of the subject invention can be inserted into the percutaneous puncture in the same manner as described earlier.

Without further elaboration the foregoing will so fully illustrate our invention that others may, by applying current or future knowledge, adopt the same for use under various conditions of service.

What is claimed is:

1. A device arranged for introduction through a percutaneous puncture into the abdomen of a living being formed during a minimally invasive surgical procedure to prevent the formation of a hernia thereat, the puncture comprising an opening in the peritoneum and a tract extending from the skin of the being to the opening, said device including a portion arranged for disposition within the puncture and constructed of a material which serves to improve the long-term strength of tissue forming at the opening when said device is in place within the puncture, said device comprising a first member, a second member, and suturing means, said first member being arranged to be extended through the tract and the opening and into engagement with the interior of the peritoneum adjacent the opening to render said first member resistant to passage back through the opening, said second member being arranged for extension through the tract outside the peritoneum and coupled to said first member and cooperating with said first member for holding said first member in engagement with the interior of the peritoneum adjacent the opening, said suturing means being coupled to said second member and operative to cause a part of said second member to penetrate tissue of the being contiguous with the tract to permanently hold said device in place within said puncture.

2. The device of claim 1 wherein said first member comprises anchoring means and said second member comprises filament means, said device additionally comprising plug means, said filament means connecting said anchoring means and said plug means together.

3. The device of claim 2 wherein said filament means connects said anchoring means to said plug means in a pulley-like arrangement.

4. The device of claim 2 wherein said plug means is deformable within the tract into a deformed state to seal the tract.

5. The device of claim 4 additionally comprising a holding member connected to said filament means, said holding member being disposed proximally of said plug means within the puncture tract and arranged to maintain said plug means in said deformed state.

6. The device of claim 1 additionally comprising reinforcing means formed of a reinforcing material, whereupon scar tissue forming at the opening is reinforced by said reinforcing material to prevent herniation of said tissue.

7. The device of claim 6 wherein said reinforcing material is non-resorbable.

8. The device of claim 6 wherein said reinforcing material comprises a mesh.

9. The device of claim 1 wherein said second member comprises filament means including a pair of ends extending out of the puncture for securement to each other adjacent the skin to hold said device in place.

10. The device of claim 9 wherein said suturing means comprises a needle, said needle being connected to one of said pair of ends to enable said one of said pair of ends to be extended through the skin contiguous with the puncture and formed into a knot with a portion of the other of said pair of ends.

11. A system for introduction through a percutaneous puncture into the abdomen of a living being formed during a minimally invasive surgical procedure, the puncture comprising an opening in the peritoneum and a tract extending from the skin of the being to the opening, said system comprising a deployment instrument and an implantable device, said device being arranged for disposition within the puncture and constructed of a material which serves to improve the long-term strength of tissue forming at the opening when said device is in place within the puncture, said device comprising a first member, a second member, and suturing means, said first member being arranged to be extended by said instrument through the tract and the opening and into engagement with the interior of the peritoneum adjacent the opening to render said first member resistant to passage back through the opening, said second member being arranged for extension through the tract outside the peritoneum and coupled to said first member and cooperating with said first member for holding said first member in engagement with the interior of the peritoneum adjacent the opening, said suturing means being coupled to said second member and operative to cause a part of said second member to penetrate tissue of the being contiguous with the tract to permanently hold said device in place within said puncture, whereupon said tissue is rendered resistant to herniation.

12. The system of claim 11 wherein said first member comprises anchoring means and said second member comprises filament means, said device additionally comprising plug means, said filament means connecting said anchoring means and said plug means together.

13. The system of claim 12 wherein said plug means is deformable within the tract into a deformed state to seal the tract and wherein said system includes tamping means extendable into said puncture to deform said plug means within the tract.

14. The system of claim 13 additionally comprising a holding member connected to said filament means, said holding member being disposed proximally of said plug means within the puncture tract and arranged to maintain said plug means in said deformed state.

15. The system of claim 12 wherein said filament means connects said anchoring means to said plug means in a pulley-like arrangement.

16. The system of claim 11 additionally comprising reinforcing means formed of a reinforcing material, whereupon scar tissue forming at the opening is reinforced by said reinforcing material to prevent the herniation of said tissue.

17. The system of claim 16 wherein said reinforcing material is non-resorbable.

18. The system of claim 11 wherein said second member comprises filament means including a pair of ends extending out of the puncture for securement to each other adjacent the skin to hold said device in place.

19. The system of claim 18 wherein said suturing means comprises a needle, said needle being connected to one of said pair of ends to enable said one of said pair of ends to be extended through the skin contiguous with the puncture and formed into a knot with a portion of the other of said pair of ends.

20. A method of preventing the formation of a hernia in an opening in the peritoneum of a living being, the opening comprising a portion of a percutaneous puncture having a tract extending from the skin of the being to the opening and being formed during a minimally invasive surgical procedure on the being, said method comprising:

(a) providing a device arranged for disposition within the puncture comprising securement means for holding said device in place within the puncture, said securement means comprising a first portion and a second portion;

(b) providing an instrument for placing said device within the puncture;

(c) using said instrument to insert said device into the puncture from the outside of the being's body so that said first portion of said securement means is extended through the tract and the opening and into engagement with the interior of the peritoneum adjacent the opening to render said first portion of said securement means resistant to passage back through the opening; and (d) causing said second portion of said securement means to be located outside the peritoneum but coupled to said first portion of said securement means and cooperating therewith for holding said device in place within the puncture, whereupon the placement of said device within the puncture prevents a hernia from forming thereat.

21. The method of claim 20 additionally comprising providing reinforcing means as a portion of said device, and wherein the placement of said device within the puncture causes said reinforcement means to be located within the puncture, whereupon any tissue forming at the opening is reinforced by said reinforcing means.

22. The method of claim 21 additionally comprising providing said reinforcing means with said first portion of said securement means through said opening so that said reinforcing means is located over the opening within the interior of the peritoneum.

23. The method of claim 21 additionally comprising providing said reinforcing means with said second portion of said securement means in the tract so that said reinforcing means is located over the opening outside of the peritoneum.

24. The method of claim 22 additionally comprising providing said reinforcing means with said second portion of said securement means in the tract so that said reinforcing means is located over the opening outside of the peritoneum.

25. The method of claim 21 additionally comprising providing said reinforcing means of a non-resorbable material.

26. The method of claim 21 additionally comprising providing said device with deformable means, disposing said deformable means within the tract to be deformed therein to close the tract.

27. The method of claim 26 additionally comprising tamping said deformable means within said tract from the outside of the puncture to deform said deformable means therein.

28. The method of claim 20 additionally comprising providing said device with filament means, extending said filament means from said device within the puncture to outside of the body of the being and securing said filament means to the skin of the being to lock the device in place.

29. The method of claim 20 additionally comprising providing said device with filament means, and securing said filament means to tissue adjacent the tract by suturing.

30. A method of strengthening tissue which forms at an opening in internal tissue within the body of a living being, the opening comprising a portion of a percutaneous puncture having a tract extending from the skin of the being to the opening and being formed during a minimally invasive surgical procedure on the being, said method comprising:

(a) providing a device arranged for disposition within the puncture to improve the long-term strength of tissue forming at the opening, said device comprising securement means for holding said device in place within said puncture, said securement means comprising a first portion and a second portion;

(b) providing an instrument for placing said device within the puncture;

(c) using said instrument to insert said device into the puncture from the outside of the being's body so that said first portion of said securement means is extended through the tract and the opening and into engagement with the interior of the internal tissue adjacent the opening to render said first portion of said securement means resistant to passage back through the opening; and (d) causing said second portion of said securement means to be located outside the internal tissue but coupled to said first portion of said securement means and cooperating therewith for holding said device in place within the puncture, whereupon the placement of said device within the puncture improves the long-term strength of tissue forming at the opening.

31. The method of claim 30 wherein said internal tissue comprises the peritoneum and wherein said method additionally comprises providing reinforcing means as a portion of said device, and wherein the placement of said device within the puncture causes said reinforcement means to be located within the puncture, whereupon any tissue forming at the opening in the peritoneum is reinforced by said reinforcing means.

32. The method of claim 31 additionally comprising providing said reinforcing means with said first portion of said securement means through said opening so that said reinforcing means is located over the opening within the interior of the peritoneum.

33. The method of claim 31 additionally comprising providing said reinforcing means with said second portion of said securement means in the tract so that said reinforcing means is located over the opening outside of the peritoneum.

34. The method of claim 32 additionally comprising providing said reinforcing means with said second portion of said securement means in the tract so that said reinforcing means is located over the opening outside of the peritoneum.

35. The method of claim 31 additionally comprising providing said reinforcing means of a non-resorbable material.

36. The method of claim 31 additionally comprising providing said device with deformable means, disposing said deformable means within the tract to be deformed therein to seal the tract.

37. The method of claim 36 additionally comprising tamping said deformable means within said tract from the outside of the puncture to deform said deformable means therein.

38. The method of claim 30 wherein said tissue comprises the lining of the thoracic cavity and wherein said method additionally comprises providing sealing means as a portion of said device, and wherein the placement of said device within the puncture seals the puncture to preclude the ingress of a fluid to the interior of the thoracic cavity.

39. The method of claim 38 additionally comprising providing said device with deformable means, disposing said deformable means within the tract to be deformed therein to seal the tract.

40. The method of claim 39 additionally comprising tamping said deformable means within said tract from the outside of the puncture to deform said deformable means therein.

41. The method of claim 38 additionally comprising providing said device with filament means, extending said filament means from said device within said puncture to outside of the body of the being and securing said filament means to the skin of the being to lock the device in place.

42. The method of claim 41 additionally comprising providing said filament means with a pair of end portions so that said end portions extend outside of the body of the being, and securing said end portions to the skin by suturing.

43. The method of claim 30 additionally comprising providing said device with filament means, extending said filament means from said device within the puncture to outside of the body of the being and securing said filament means to the skin of the being to lock the device in place.

44. The method of claim 30 additionally comprising providing said device with filament means, and securing said filament means to tissue adjacent the tract by suturing.

45. A method of repairing internal tissue within the body of a living being, said method comprising:
(a) creating a percutaneous puncture to said internal tissue, said puncture having an opening in said tissue and a tract extending from the skin of the being to the opening;
(b) providing a device arranged for disposition within the puncture comprising securement means for holding said device in place within the puncture, said securement means comprising a first portion and a second portion;
(c) providing an instrument for placing said device within the puncture;
(d) using said instrument to insert said device into the puncture from the outside of the being's body so that said first portion of said securement means is extended through the tract and the opening and into engagement with the interior of the internal tissue adjacent the opening to render said first portion of said securement means resistant to passage back through the opening; and
(e) causing said second portion of said securement means to be located outside the internal tissue but coupled to said first portion of said securement means and cooperating therewith for holding said device in place within the puncture, whereupon the placement of said device within the puncture prevents a hernia from forming thereat.

46. A device arranged for introduction through a percutaneous puncture into the thoracic cavity of a living being formed during a minimally invasive surgical procedure to prevent the leakage of air therein, the puncture comprising an opening in the thoracic cavity wall and a tract extending from the skin of the being to the opening, said device including a first member, a second member, and suturing means, said first member being arranged to be extended through the tract and the opening and into engagement with the interior of the thoracic wall adjacent the opening to render said first member resistant to passage back through the opening, said second member being arranged for extension through the tract outside the thoracic wall and coupled to said first member and cooperating with said first member for holding said first member in engagement with the interior of the thoracic wall adjacent the opening, said suturing means being coupled to said second member and operative to cause a part of said second member to penetrate tissue of the being contiguous with the tract to permanently hold said device in place within said puncture, whereupon said device seals the puncture to prevent air from gaining ingress to the thoracic cavity through the puncture.

47. The device of claim 46 wherein said first member comprises anchoring means and said second member comprises filament means, said device additionally comprising plug means, said filament means connecting said anchoring means and said plug means together.

48. The device of claim 47 wherein said plug means is deformable within the tract into a deformed state to seal the tract.

49. The device of claim 47 wherein said anchoring means comprises an elongated, substantially stiff member.

50. The device of claim 47 wherein said anchoring means is formed of a resorbable material.

51. The device of claim 47 wherein said anchoring means includes reinforcing means formed of a reinforcing material, whereupon scar tissue forming at the opening is reinforced by said reinforcing material to prevent the herniation of said tissue.

52. A system for introduction through a percutaneous puncture into the thoracic cavity of a living being formed during a minimally invasive surgical procedure to seal the puncture to prevent air from gaining ingress to the thoracic cavity through the puncture, the puncture comprising an opening in the wall of the thoracic cavity and a tract extending from the skin of the being to the opening, said system comprising a deployment instrument and an implantable device, said device comprising a first member, a second member, and suturing means, said first member arranged to be extended by said instrument through the tract and the opening for engaging the interior of the thoracic wall adjacent the opening to render said first member resistant to passage back through the opening, said second member being arranged for extension through the tract outside the thoracic wall and coupled to said first member and cooperating with said first member for holding said first member in engagement with the interior of the thoracic cavity adjacent the opening, said suturing means being coupled to said second member and operative to cause a part of said second member to penetrate tissue of the being contiguous with the tract to permanently hold said device in place within the puncture, whereupon the puncture is sealed to prevent air from gaining ingress to the thoracic cavity through the puncture.

53. The system of claim 52 wherein said first member comprises anchoring means and said second member comprises filament means, said device additionally comprising plug means, said filament means connecting said anchoring means and said plug means together.

54. The system of claim 53 wherein said plug means is deformable within the tract into a deformed state to seal the tract.

55. The system of claim 52 wherein said anchoring means comprises an elongated, substantially stiff member.

56. The system of claim 52 wherein said anchoring means is formed of a resorbable material.

57. The device of claim 52 wherein said anchoring means includes reinforcing means formed of a reinforcing material, whereupon scar tissue forming at the opening is reinforced by said reinforcing material to prevent the herniation of said tissue.

58. A method of sealing a percutaneous puncture extending into the thoracic cavity of a living being to prevent the leakage of air through the puncture, the percutaneous puncture having an opening in the thoracic wall and a tract extending from the skin of the being to the opening and being formed during a minimally invasive surgical procedure on the being, said method comprising:

(a) providing a device arranged for disposition within the puncture, said device comprising securement means for holding said device in place within the puncture, said securement means comprising a first portion, a second portion, and a filament portion;

(b) providing an instrument for placing said device within the puncture;

(c) using said instrument to insert said device into said puncture from the outside of the being's body so that said first portion of said securement means is extended through the tract and the opening and into engagement with the interior of the thoracic wall adjacent the opening to render said first portion of said securement means resistant to passage back through the opening;

(d) causing said second portion of said securement means to be located outside the thoracic wall but coupled to said first portion of said securement means by said filament means and cooperating therewith for holding said device in place within said puncture; and (e) causing a portion of said filament means to penetrate tissue of the being contiguous with the puncture to fixedly secure said device in place, whereupon the placement and securement of said device within the puncture seals the puncture to prevent the leakage of air into the thoracic cavity.

59. The method of claim 58 wherein said first portion of said device comprises anchoring means and said second portion of said device comprises plug means, said filament means connecting said anchoring means and said sealing means together, and wherein method comprises locating said plug means within said tract.

60. The method of claim 59 wherein said plug means is deformable, and wherein said method additionally comprises deforming said plug means within the tract so that said plug means is in a deformed state to seal the tract.

61. The method of claim 59 wherein said method additionally comprises providing reinforcing means with said anchoring means, said reinforcing means being formed of a reinforcing material.

\* \* \* \* \*